(12) United States Patent
Ueno

(10) Patent No.: US 6,414,016 B1
(45) Date of Patent: Jul. 2, 2002

(54) ANTI-CONSTIPATION COMPOSITION

(75) Inventor: Ryuji Ueno, Potomac, MD (US)

(73) Assignee: Sucampo, A.G., Zurich (GH)

( * ) Notice: Subject to any disclaimer, the term of this patent is extended or adjusted under 35 U.S.C. 154(b) by 0 days.

(21) Appl. No.: 09/655,760

(22) Filed: Sep. 5, 2000

(51) Int. Cl.$^7$ ............................................... A61K 31/35
(52) U.S. Cl. ..................................................... 514/456
(58) Field of Search ......................................... 514/456

(56) References Cited

U.S. PATENT DOCUMENTS 5,317,032 A 5/1994 Ueno et al.

FOREIGN PATENT DOCUMENTS

| EP | 0 310 305 A | 4/1989 |
|---|---|---|
| WO | WO 01/25099 A | 4/2001 |

OTHER PUBLICATIONS

Hawley, G, Condensed Chemical Dictionary, 10th edition, 1981, p. 996.*

* cited by examiner

Primary Examiner—Rebecca Cook
(74) Attorney, Agent, or Firm—Sughrue Mion, PLLC

(57) ABSTRACT

An object of the present invention is to provide an anti-constipation composition containing a halogenated-bi-cyclic compound as an active ingredient in a ratio of bi-cyclic/mono-cyclic structure of at least 1:1. The halogenated-bi-cyclic compound is represented by Formula (I):

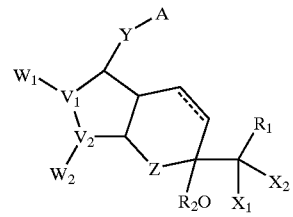

where $X_1$ and $X_2$ are preferably both fluorine atoms. The composition can be used to treat constipation without substantive side-effects, such as stomachache.

13 Claims, No Drawings

ANTI-CONSTIPATION COMPOSITION

TECHNICAL FIELD

The present invention relates to a novel therapeutic composition that contains halogenated bi-cyclic structures for treatment of constipation and use thereof.

BACKGROUND OF THE INVENTION

Prostaglandins (hereinafter referred to as PGs) is the name of the group of fatty acids which possess various physiological activities and contained in human and animal tissues and organs. PGs basically contain the prostanoic acid skeleton of the following formula:

and some synthetic products may contain the above skeleton with some modification. PGs are classified into several types according to the structure and substituents on the five-membered ring, for example, Prostaglandins of the A series (PGAs)

Prostaglandins of the B series (PGBs)

Prostaglandins of the C series (PGCs)

Prostaglandins of the D series (PGDs)

Prostaglandins of the E series (PGEs)

Prostaglandins of the F series (PGFs)

and the like. Further, they are classified into $PG_1$s containing a 13,14-double bond; $PG_2$s containing, 5,6- and 13,14-double bonds; and $PG_3$s containing 5,6-, 13, 14- and 17,18-double bonds.

PGs are expressed as follows. In PGs, the carbons constituting an α-chain, an ω-chain and a five-membered ring are numbered according to the basic skeleton as follows:

That is, in the basic skeleton, the constituent carbon atoms are numbered in such a way that the carbon atom in the carboxyl group is C-1, and the cc-chain contains C-2–C-7, the number increasing toward the ring, the five-membered ring contains C-8–C-12, and the ω-chain contains C-13–C-20. When the carbons of α-chain are fewer, the numbers of the carbon atoms ensuing C-2 should be properly shifted, and when more than 7, the compound is named provided that carbon at the C-2 position has substituent instead of carboxyl group (at the C-1 position). When the ω-chain contains fewer carbon atoms they should be numbered correspondingly smaller than 20, and when more than 8, the carbon atoms at the 21 position and thereafter should be regarded as a substituent. As configuration, it is considered according to that of the above essential skeleton unless otherwise described.

For example, PGD, PGE and PGF mean compounds having hydroxyl group at the C-9 and/or C-11 positions. In the present invention, PGs also include those having other group instead of the hydroxyl group on the C-9 and/or C-11-positions, they being named as 9-dehydroxy-9-substituted or 11-dehydroxy-11-substituted compounds.

In addition, PGs may include the isomers, such as bi-cyclic tautomers, optical isomers; geometrical isomers, or the like.

PGs are known to have various pharmacological and physiological activities, for example, vasodilation, inducing of inflammation, platelet aggregation, stimulating uterine muscle, stimulating intestinal muscle, anti-ulcer effect and the like. PGEs or PGFs are found to possess contraction of intestines caused by intestinal stimulation is great, while enteropooling effect is poor. Accordingly, it is impossible to use PGEs or PGFs as cathartics because of side effects such as stomachache caused by the intestinal contraction.

On the other hand, PGs having a 13,14-single bond and a C-15 constituting carbonyl group, and those having a 13,14-double bond and a C-15 constituting carbonyl group are found to exist in human or animal metabolites. These 13,14-dihydro-15-keto-prostaglandins and 15-keto-prostaglandins (hereinafter referred to as 15-keto-PGs) are known to be naturally produced metabolites by enzymatic metabolism of the corresponding PGs in vivo. These 15-keto-PGs have been reported to hardly exhibit various physiological activities that PGs possess and be pharmacologically and physiologically inactive metabolites [see, Acta Physiologica Scandinavica, 66, p.509-(1966)].

U.S. Pat. No. 5,317032 to Ueno et al. describes prostaglandin cathartics, including the existence of bi-cyclic tautomers. However, the pronounced activity as anti-constipation treatment and prevention agents of the bi-cyclic tautomers has not been heretofore known.

While estimating the pharmacological activities of the analogues of 15-keto-PGs, however, the present inventors have found that the corresponding bi-cyclic compounds, i.e., the bi-cyclic tautomers, substituted by one or more halogen atoms can be employed in small doses for relieving constipation. At the C-16 position, especially, fluorine atoms, can be employed in small doses for relieving constipation. Where desired, larger doses to cause strong cathartic effect can be employed, although the primary purpose of the present invention is to restore a normal number of bowel movements (3 to 7 per week).

SUMMARY OF THE INVENTION

An object of the present invention is to provide a composition for treatment of constipation comprising bi-cyclic-halogenated compounds without substantive side effects such as stomachache caused by intestinal contraction. Accordingly, the bi-cyclic-halogenated compounds of the present invention may be used not only for treatment of chronic or intermittent constipation, but also for treatment or prevention of constipation (as well as to effect loose bowels when desired) in the patients suffering from constipation associated with, for example, in hernia or cardiovascular system disease, in order not to strain at stool, or suffering from proctogenic diseases. Moreover, they may be used to produce normal bowel movements for washing out harmful substances from intestine in case of drug or food poisoning. Additionally, the bi-cyclic halogenated compounds may be used as a bowel cleansing agent used for preparation of the bowel prior to preventative, diagnostic or surgical procedures.

DETAILED DESCRIPTION OF THE INVENTION

The present invention provides an anti-constipation composition (prevention and/or treatment of constipation) containing bi-cyclic-halogenated compounds as active ingredients.

Cathartics work by the combination of one or more of the four mechanisms shown below, thereby increasing water content of feces and promoting transfer of the content in the intestines:

(i) Water and electrolytes may be kept in intestines owing to the hydrophilicity or osmotic pressure of the drug, thereby the intraintestinal content increased in volume which indirectly results in faster transfer thereof.

(ii) The drug may work on the intestinal mucosa to reduce total amount of normal absorption of electrolytes and water and increase the amount of water, indirectly resulting in faster transfer of the intraintestinal content.

(iii) The drug may work on the intestinal mucosa to increase total amount of normal secretion of electrolytes and water and increase the amount of water, directly and/or indirectly resulting in faster transfer of the intraintestinal content.

(iv) The drug firstly works on intestinal movement to fasten transfer, indirectly resulting in reduced net absorption of water and electrolytes because the time for them to be absorbed is reduced.

The enteropooling test employed in the present invention is intended to investigate mainly on the action (ii) and/or (iii), which assesses the effect of the drug on the intraintestinal water pool by measuring the volume of the intraintestinal content. The bi-cyclic-halogenated compounds of the present invention may show extremely great enteropooling effect. However, they hardly or slightly cause contraction of intestines which is one of indexes for assessment of the action (iv). Accordingly, the bi-cyclic-halogenated compounds of the present invention are considered to alleviate constipation by mainly acting on intestinal mucosa directly or indirectly to affect transfer of electrolytes and water from intestinal walls into blood vessels and/or from blood vessels into intestines, resulting in reduced water absorption and/or in increased water secretion through the intestines, increased intraintestinal water pool and promoted transfer of the intraintestinal content.

A preferred compound used in the present invention is represented by formula (I):

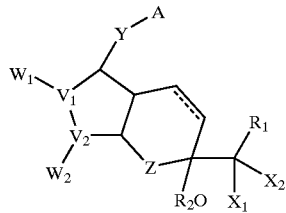

Formula (I)

where $V_1$ and $V_2$ are carbon or oxygen atoms;
$W_1$ and $W_2$ are

$R_3$ and $R_4$ are both hydrogen atoms or one of them is OH;

$X_1$ and $X_2$ are hydrogen, lower alkyl or halogen atom, and at least one of these is a halogen atom;

Z is a carbon, oxygen, sulfur or nitrogen atom;

$R_2$ is a hydrogen atom or lower alkyl;

Y is a saturated or unsaturated $C_{2-10}$ hydrocarbon chain which is unsubstituted or substituted by oxo, halogen, an alkyl group, hydroxyl or aryl;

A is -$CH_2OH$, -$COCH_2OH$, -COOH or its functional derivative; and $R_1$ is a saturated or unsaturated, lower hydrocarbon forming a straight-chain, a branched-chain or a ring, which is unsubstituted or substituted by halogen, oxo, hydroxy, lower alkoxy, lower alkanoyloxy, lower cycloalkyl, lower cycloalkyloxy, aryl, or aryloxy. Preferably $R_1$ is not substituted. Where a substituent is present, care must be exercised to avoid possible steric hinderance in formation of the bi-cyclic compound from or in association with the corresponding monocyclic PGs.

The steric configuration of C-15 can be R, S, or a mixture thereof.

The bond between C-13 and C-14 position can be a single or double bond.

In the above formula, the term "unsaturated" is intended to include at least one or more double bonds and/or triple bonds that are isolatedly, separately, or serially present between the carbon atoms of the main and/or side chains. An unsaturated bond between two serial positions is represented by denoting the lower number of the two positions, and an unsaturated bond between two distal positions is represented by denoting both of the positions.

Preferred unsaturated bonds are a double at position 2 and a double or triple bond at position 5.

The term "lower" is intended to include a group having 1 to 8 carbon atoms, unless otherwise specified.

The term "ring" includes lower cycloalkyl, lower cycloalkoxy, aryl or aryloxy.

The term "halogen" includes fluorine, chlorine, bromine, or iodine atom. Particularly preferable is a fluorine atom.

The term "lower alkoxy" refers to a group of lower alkyl-O—, wherein lower alkyl is a straight or branched chain saturated hydrocarbon group containing 1 to 6 carbon atoms and includes, for example, methyl, ethyl, propyl, isopropyl, buyl, isobutyl, t-butyl, pentyl and hexyl.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO—is an acyl group formed by oxidation of a lower alkyl group as defined above, such as acetyl.

The term "lower cycloalkyl" refers to a cyclic group formed by cyclization of a lower alkyl group as defined above but contains three or more carbon atoms, and includes, for example, cyclopropyl, cyclobutyl, cyclopentyl and cyclohexyl.

The term "lower cycloalkyloxy" refers to the group of lower-cycloalkyl-O—, wherein lower cycloalkyl is as defined above.

The term "aryl" may include unsubstituted or substituted aromatic carbocyclic or heterocyclic groups (preferably mono-cyclic groups), for example, phenyl, naphthyl, tolyl, xylyl, furyl, thienyl, pyrrolyl, oxazolyl, isoxazolyl, thiazolyl, isothiazolyl, imidazolyl, pyrazolyl, furzanyl, pyranyl, pyridyl, pyridazyl, pyrimidryl, pyrazyl, pyrrolidinyl, imidazolidinyl, pyrazolidinyl, piperidino, piperazinyl, morpholono, indolyl, benzothienyl, quinolyl, isoquinolyl, puryl, quinazolinyl, carbazolyl, acridinyl, phenathridinyl, benzimidazolyl, benzimidazolonyl, benzothiazolyl and phenothiazinyl. Examples of substituents are halogen atom and halo(lower)alkyl, wherein halogen atom and lower alkyl are as defined above.

The term "aryloxy" refers to a group represented by the formula Ar—O, wherein Ar is aryl as defined above.

The bi-cyclic-16-halogen compounds used in the present invention may be salts or those with an esterified carboxyl group or etherified group. Such salts include pharmaceutically acceptable salts, for example, those of alkali metals such as sodium, potassium; those of alkaline earth metals such as calcium, magnesium; those of physiologically acceptable ammonium salts such as ammonia, methylamine, dimethylamine, cyclopentylamine, cyclohexylamine, benzylamine, piperidine, ethylenediamine, monoethanolamine, diethanolamine, triethanolamine, monomethylmonoethanolamine, trometamine, lysine, procaine, caffeine, arginine, tetralkylammonium salt and the like. These salts may be prepared by a conventional process, for example, from the corresponding acid and base or by salt interchange.

Such esters and ethers include, for example, straight or branched alkyl esters and ethers which may contain one or more unsaturated bonds such as methyl, ethyl, propyl, butyl, isopropyl, isobutyl, t-butyl, pentyl, 2-ethylhexyl; those having an alicyclic group such as a cyclopropyl, cyclopentyl or cyclohexyl group; those containing an aromatic group such as a benzyl or phenyl group (wherein the aromatic group may contain one or more substituents); a lower alkenyl such as ethynyl and propynyl, hydroxyalkyl or alkoxyalkyl such as hydroxyethyl, hydroxyisopropyl, polyhydroxyethyl, polyhydroxyisopropyl, methoxyethyl, ethoxyethyl or methoxyisopropyl ester or ether; optionally substituted aryls such as phenyl, tosyl, t-butylphenyl, salicyl, 3,4-dimethoxyphenyl and benzamidophenyl; alkylsilyls such as a trimethylsilyl or triethylsilyl; or a tetrahydropyranyl ester or ether.

Preferred esters and ethers include, for example, straight-chain or branched lower alkyl such as methyl, ethyl, propyl, n-butyl, isopropyl or t-butyl; a benzyl; or hydroxyalkyl such as a hydroxyethyl or hydroxyisopropyl.

Preferred A is —COOH or its pharmaceutically acceptable salt or ester.

Preferred $X_1$ and $X_2$ are both being halogen atoms, and more preferably, fluorine atoms.

Preferred $W_1$ is =O.

Preferred $W_2$ is where $R_3$ and $R_4$ are both hydrogen atoms.

Preferred Z is an oxygen atom.

Preferred Y is an unsubstituted saturated or unsaturated hydrocarbon chain having 6–8 carbon atoms.

Preferred $R_1$ is an unsubstituted saturated or unsaturated hydrocarbon chain having 4–8 carbon atoms.

$R_2$ is preferably a hydrogen atom.

The composition of the present invention may include the isomers of the above compounds. Examples of such isomers include mono-cyclic tautomers having a keto group at the C-15 position and halogen at the C-16 position; optical isomers; geometrical isomers and the like.

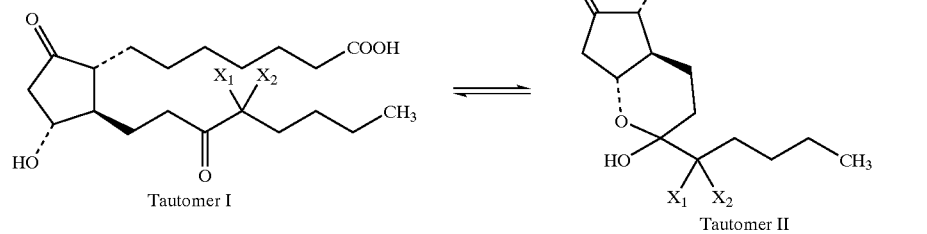

Tautomer I ⇌ Tautomer II

The tautomerism between the oxygen atom at the C-11 position and the keto group at the C-15 position, shown above, is especially significant in the case of compounds having a 13,14-single bond and two fluorine atoms at the C-16 position.

It has been discovered that in the absence of water, compounds represented by Formula (I) exist predominantly in the form of the bi-cyclic compound. In aqueous media, it is believed that hydrogen bonding occurs between, for example, the ketone position at the C-15 position, thereby hindering bi-cyclic ring formation. In addition, it is believed that the halogen atom(s) at the C-16 position promote bi-cyclic ring formation. The mono-cyclic/bi-cyclic structures, for example, may be present in a ratio of 1:6 in $D_2O$; 1:10 in $CD_3OD$-$D_2O$ and 4:96 in $CDCl_3$. Accordingly, a preferable embodiment of the present invention is the composition in which the bi-cyclic form is present in ratio of bi-cyclic/mono-cyclic of least 1:1, and preferably 20:1, or even greater to substantially all bi-cyclic compound; 100% bi-cyclic compound is within this invention.

The above described bi-cyclic-16-halogen compound may prepared according to the general process set forth below:

Preparation of Isopropyl 7-[(1S,3S,6S,7R)-3-Heptyl-3-hydroxy-bi-cyclo[4.3.0]nonane-8-one-7-yl] hept-5-enoate and Isopropyl 7-[1R,3S,6S,7R)-3-heptyl-3-hydroxy-bicyclo[4.3.0]nonane-8-one-7-yl] hept-5-enoate 1. Preparation of Isopropyl (Z)-7-[1R,2R,3R,5S)-2-(3,3-Ethylenedioxydecyl)-5-hydroxy-3-(p-toluensulfonyl)cyclopentyl]hept-5-enoate (2)

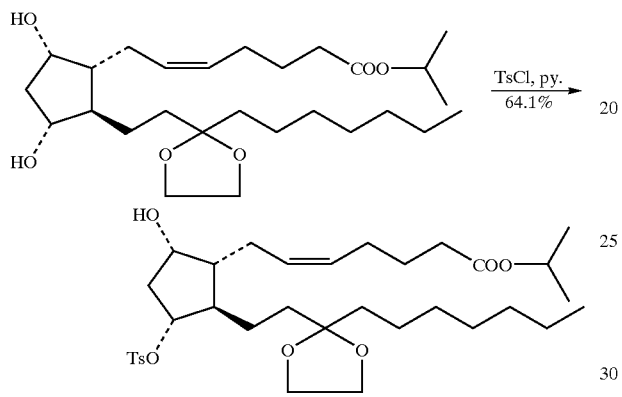

To a mixture of pyridine (0.77g) and isopropyl(Z)-7-[(1R,2R,3R,5S)-3,5-dihydroxy-2-(3,3-ethylenedioxydecyl)cyclopentyl]hept-5-enoate (1) (4.05 g) in dichloromethane, a solution of tosyl chloride (1.86 g) in dichloromethane was added at 0° C., and stirred for 2 days at the temperature. During the reaction, each tosyl chloride (5.58 g) and pyridine (2.31 g) was added in three portions. After the usual work-up, the crude product was chromatographed on silica gel to give isopropyl (Z)-7-[(1R,2R,3R,5S)-2-(3,3-ethylenedioxydecyl)-5-hydroxy-3-(p-toluenesulfoxy)cyclopentyl]hept-5-enoate (2). Yield 3.45 g, 64.1%.

2. Preparation of Isopropyl (Z)-7-[(1R,2S)-2-(3,3-Ethylenedioxydecyl)-5-oxocyclopent-3-enyl]hept-5-enoate (3)

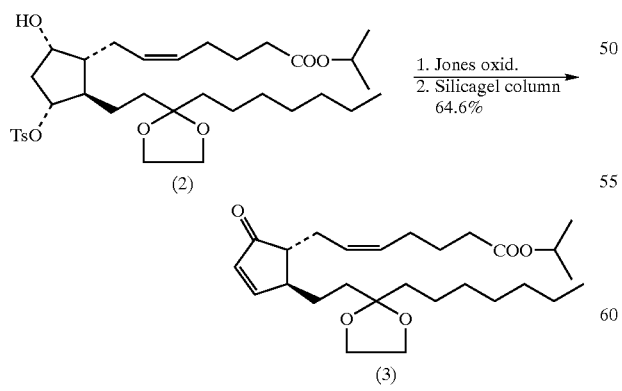

Isopropyl (Z)-[1R,2R,3R,5S)-2-(3,3-ethylenedioxydecyl)-5-hydroxy-3-(p-toluenesulfoxy)cyclopentyl]hept-5-enoate (2) (1.72 g) was oxidized in acetone at −40° C. to −20 C. with Jones reagent for 4 hours. After the usual work-up, the crude product was passed through silica gel pad with n-hexane/ethyl acetate (3.5/1). The product was further chromatographed on silica gel (n-hexane/ethyl acetate =4/1). Isopropyl (Z)-7-[(1R,2S)-2-(3,3-ethylenedioxydecyl)-5-oxo-cyclopent-3-enyl]hept-5-enoate (3) was obtained. Yield 0.81 g, 64.6%.

3. Preparation of Isopropyl-7-[(1R,2S,3R)-2-(3,3-Ethylenedioxydecyl)-3-hydroxymethyl-5-oxocyclopentyl] hept-5-enoate (4)

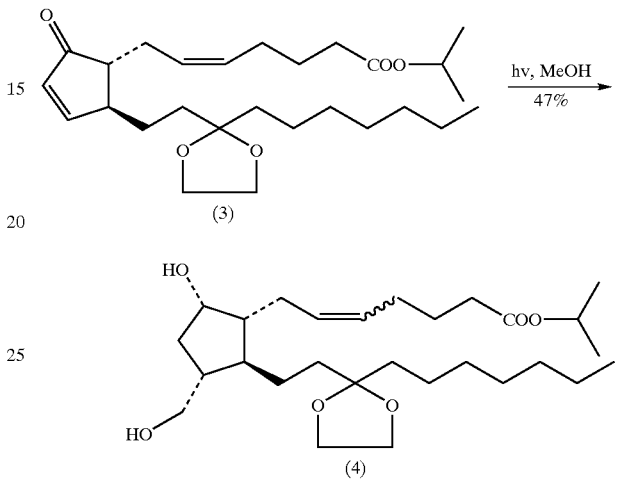

Isopropyl (Z)-7-[(1R,2S)-2-(3,3-ethylenedioxydecyl)-5-oxo-cyclopent-3-enyl]hept-5-enoate (3) (0.81 g) and benzophenone were dissolved in methanol. Under argon atmosphere, the solution was irradiated with 300-W high-pressure mercury lamp for 4 hours and 40 minutes. After evaporation of the solvent, the crude product was chromatographed on silica gel (n-hexane/ethyl acetate =3/2) to give isopropyl-7-[(1R,2S,3R)-2-(3,3-ethylenedioxydecyl)-3-hydroxymethyl-5-oxocyclopentyl]hept-5-enoate (4). Yield 0.41 g, 47%.

4. Preparation of Isopropyl-7-[1R,2S,3R)-2-(3,3-Ethylenedioxydecyl)-5-oxo-3-(p-toluenesuffoxymethyl)cyclopentyl]hept-5-enoate (5)

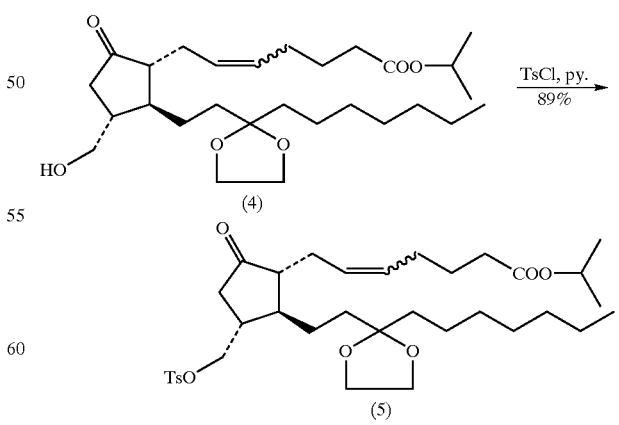

Isopropyl-(1R,2S,3R)-2-(3,3-ethylenedioxydecyl)-3-hydroxymethyl-5-oxocyclopentyl]hept-5-enoate (4) (0.21 g) and pyridine (0.07 g) were dissolved in dichloromethane. To this solution, tosyl chloride (0.17 g) was added at 0° C., and the mixture was stirred for 72 hours. After the usual work-up, the crude product was chromatographed on silica gel to give isopropyl 7-(1R,2S,3R)-2-(3,3-ethylenedioxydecyl)-5-oxo-3-(p-toluenesulfoxy)methylcyclopentyl]hept-5-enoate (5). Yield 0.25 g, 89%.

5. Preparation of Isopropyl-7-[(1R,2R,3R)-2-(3,3-Ethylenedioxydecyl)-3-iodemethyl-5-oxocyclopentyl]hept-5-enoate (6)

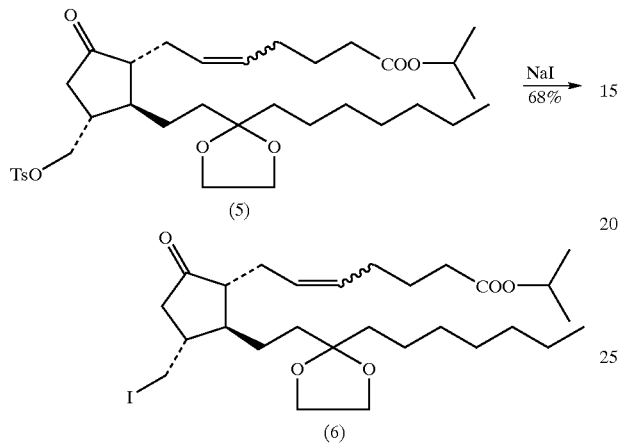

Isopropyl 7-(1R,2S,3R)-2-(3,3-ethylenedioxydecyl)-5-oxo-3-(p-toluenesulfoxy)methylcyclopentyl]hept-5-enoate (5) (0.25 g) was dissolved in acetone, and sodium iodide (0.12 g) was added. The mixture was refluxed for 3 hours. Sodium iodide (0.097 g) was added to the mixture, and the mixture was refluxed for additional 80 minutes. After the usual work-up, the crude product was chromatographed on silica gel (n-hexane/ethyl acetate =5/1) to give isopropyl 7-(1R,2R,3R)-2-(3,3-ethylenedioxydecyl)-3-iodemethyl-5-oxocyclopentyl]hept-5-enoate (6). Yield 0.16 g, 68%.

6. Preparation of Isopropyl 7-(1R,2R,3R)-3-Iodemethyl-5-oxo-2-(3-oxodecyl)cyclopentyl]hept-5-enoate (7)

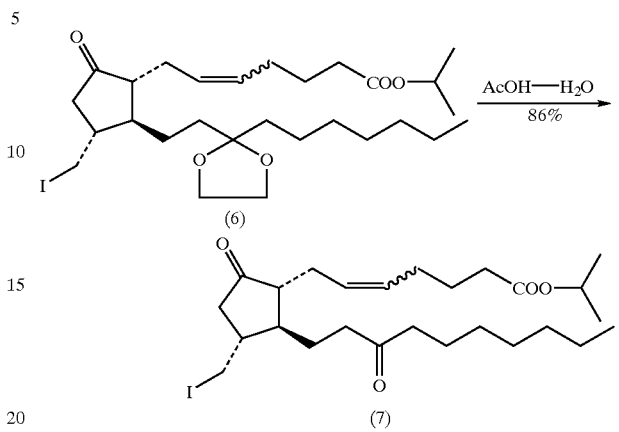

Isopropyl 7-(1R,2R,3R)-2-(3,3-ethylenedioxydecyl)-3-iodemethyl-5-oxocyclopentyl]hept-5-enoate (6) (0.16 g) was dissolved in a mixed solvent of acetic acid/water/tetrahydrofuran (3/1/1). The mixture was stirred for 20 hours at room temperature and for 2.5 hours at 50° C. After evaporation of the solvent, the obtained residue was chromatographed on silica gel (n-hexane/ethyl acetate=1/1) to give isopropyl 7-(1R,2R,3R)-3-iodemethyl-5-oxo-2-(3-oxodecyl)cyclopentyl]hept-5-enoate (7). Yield. 0.13 g; 86%.

7. Preparation of Isopropyl 7-(1S,3S,6S,7R)-3-Heptyl-3-hydroxy-bicyclo[4.3]nonane-8-one-7-yl]hept-5-enoate (8a) and Isopropyl 7-(1S,3R,6S,7R)-3-heptyl-3-hydroxy-bicyclo[4.3.0]nonane-8-one-7-yl]hept-5-enoate (8b)

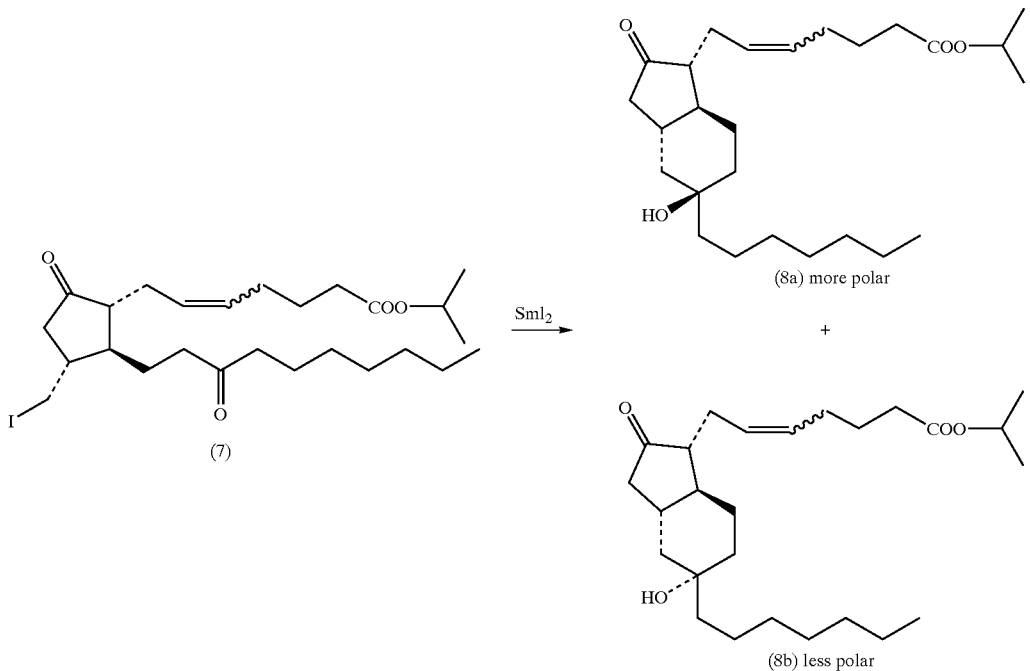

Isopropyl 7-(1R,2R,3R)-3-iodemethyl-2-(3-oxodecyl)-5-oxocyclopentyl]hept-5-enoate (7) (0.0574 g) and zirconocene dichloride were dissolved in tetrahydrofuran. The mixture was sonicated under argon stream to purge the air out from the mixture. To the mixture samarium iodide in tetrahydrofuran (0.1 M, 2.1 mL) was added dropwise. The mixture was stirred for 30 minutes at room temperature, and then hydrochloric acid (0.1M, 1 mL) was added. After the usual work-up, the crude product was chromatographed on silica gel (n-hexane/ethyl acetate=5/1). Two bicyclic products, more polar (8a) and its epimer, less polar (8b) and starting material (7) were obtained as follows:

Isopropyl 7-(1S,3S,6S,7R)-3-heptyl-3-hydroxy-bicyclo[4.3.0]nonane-8-one-7-yl]hept-5-enoate (8a) and Isopropyl 7-(1S,3R,6S,7R)-3-heptyl-3-hydroxy-bicyclo[4.3.0]nonane-8-one-7-yl]hept-5-enoate (8b): Yield 8(a) 5.1 mg, Yield 8(b) 7.2 mg, Recovery of starting material (7) 26.7 mg.

A theoretical synthesis for a compound represented by Formula (I) where Z is a sulfur atom and $W_1$ is an —OH group is set forth below:

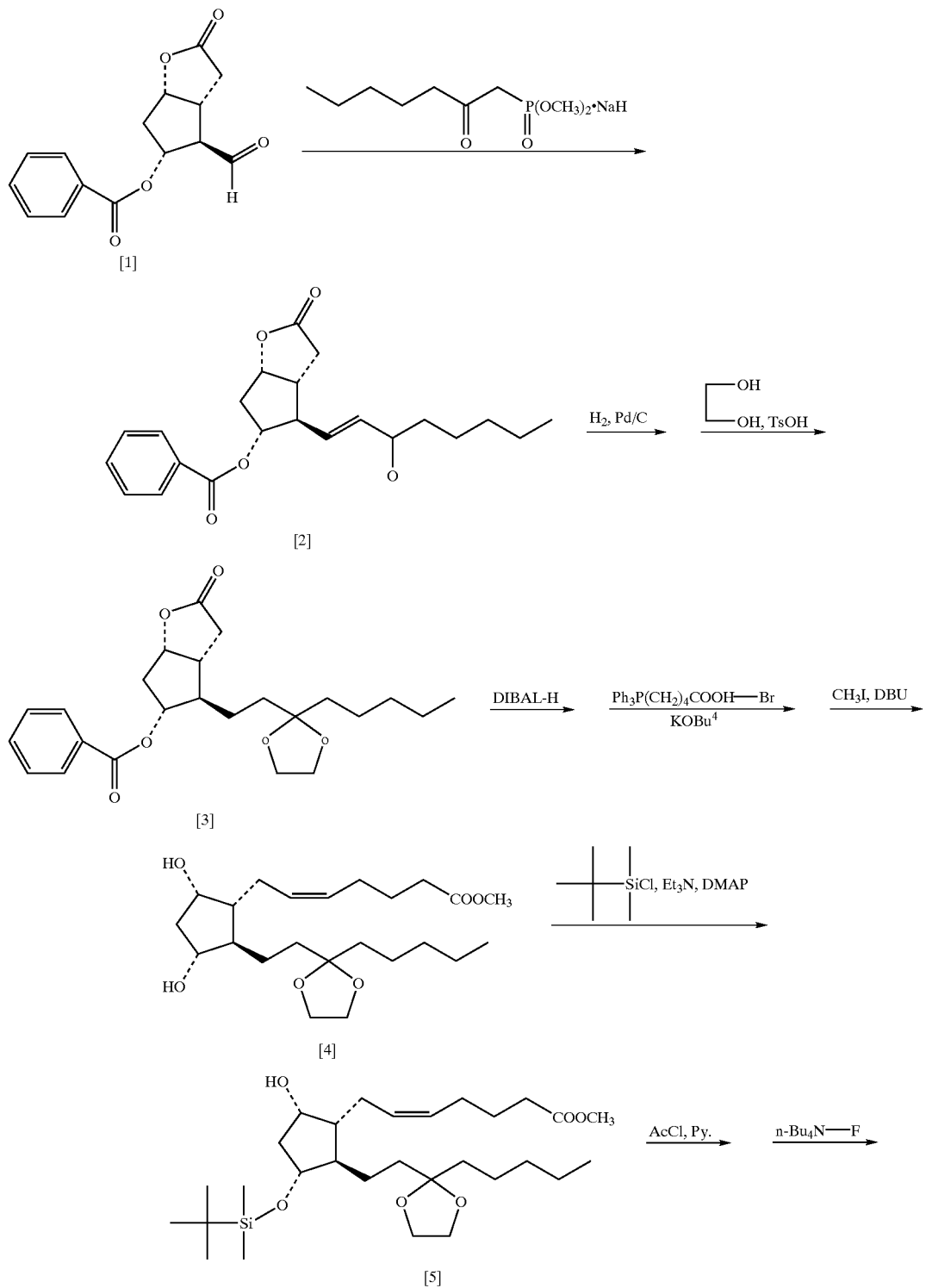

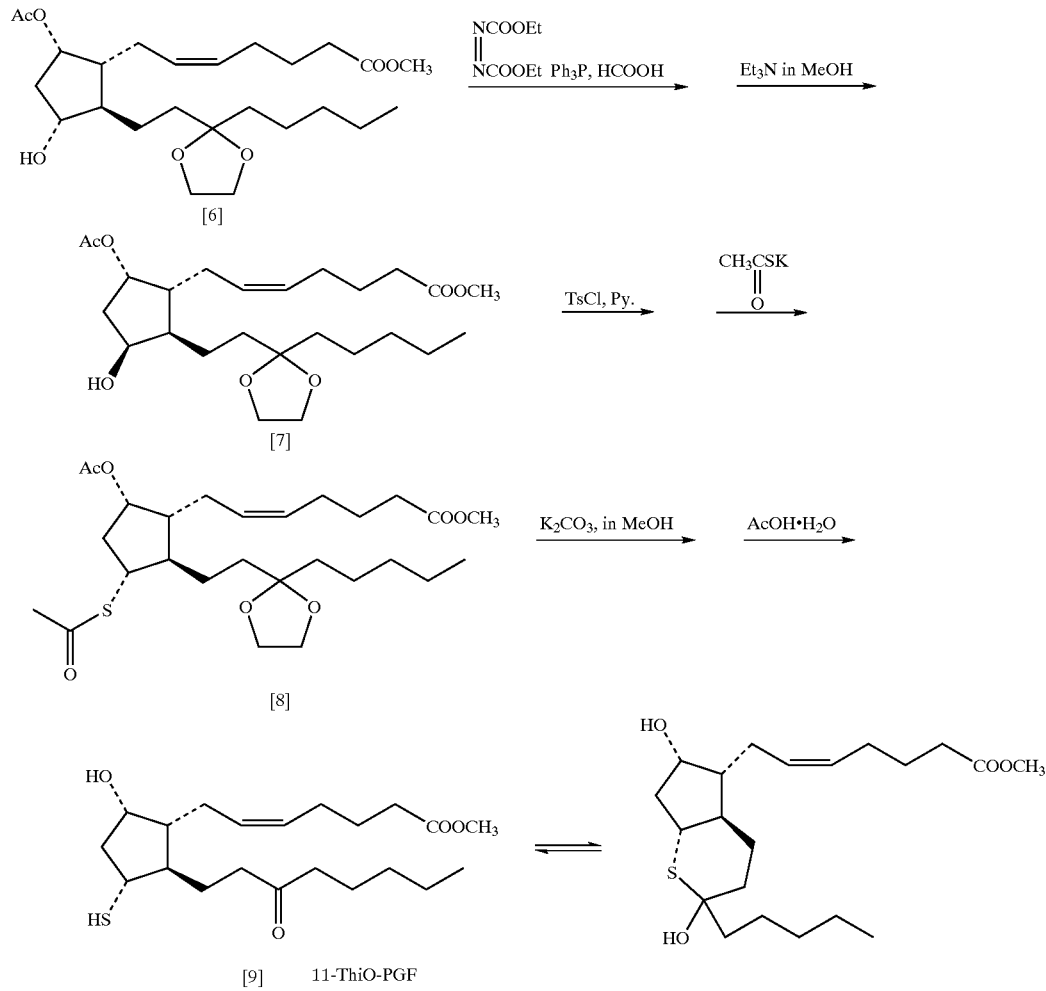
n-Bu₄N—F: tetrabutylammonium fluoride
DBU: 1,8-diazabicyclo[5.4.0]undec-7-ene
DIBAL-H: diisobutylaluminum hydride
DMAP: 4-dimethylaminopyridine
NaBH₄: sodium borohydride
A theoretical synthesis for a compound represented by Formula (I) where Z is a sulfur atom and $W_1$ is a keto is set forth below:
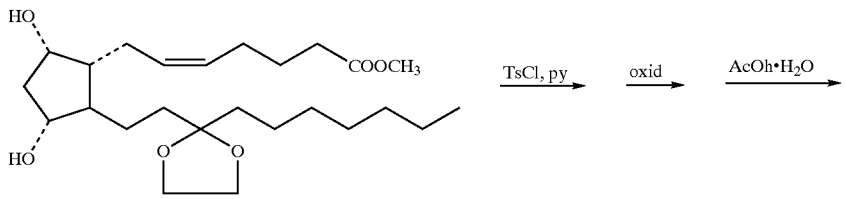

-continued
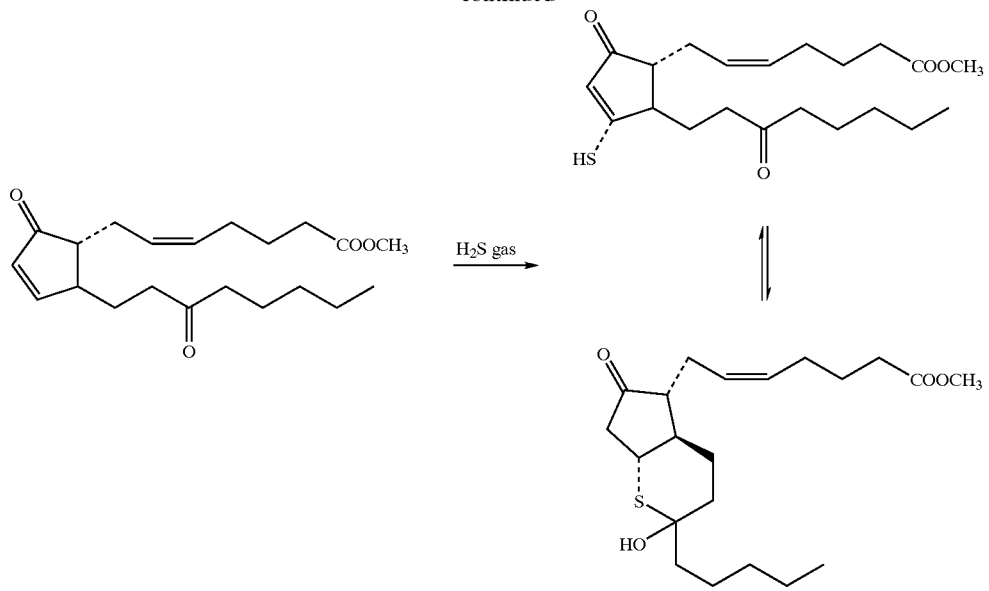
A theoretical synthesis for a compound represented by Formula (I) where Z is a sulfur atom, $W_1$ is a keto and $X_1$ and $X_2$ are fluorine atoms is set forth below:
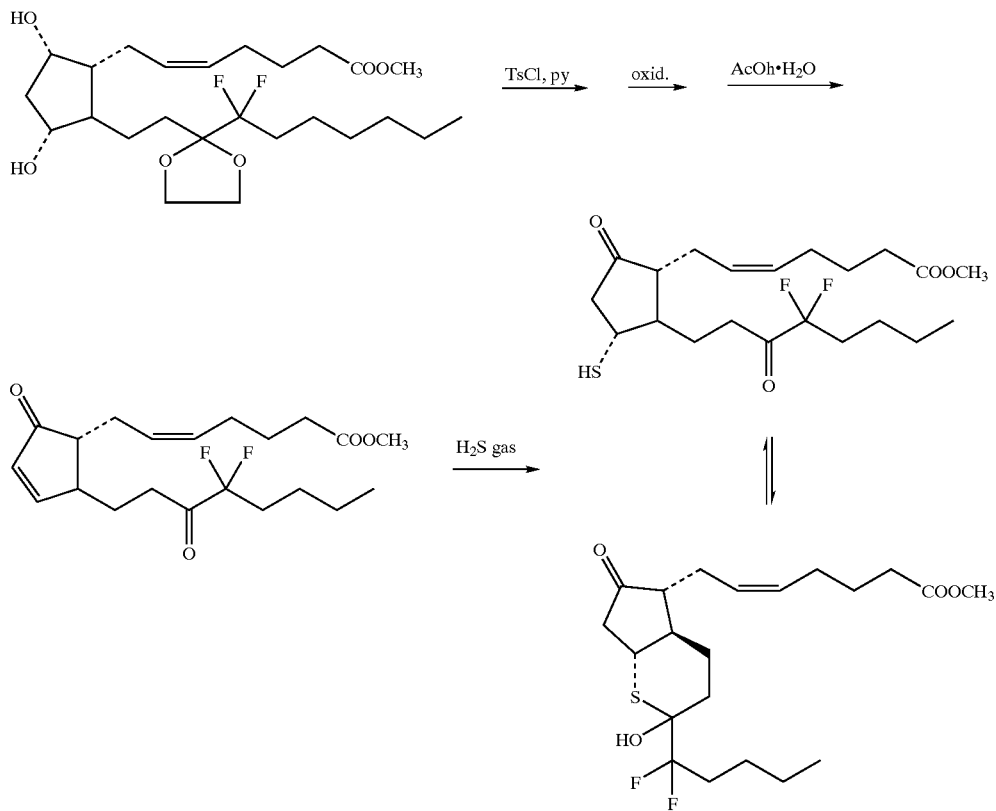
A theoretical synthesis for a compound represented by Formula (I) where Z is a nitrogen atom is set forth below:

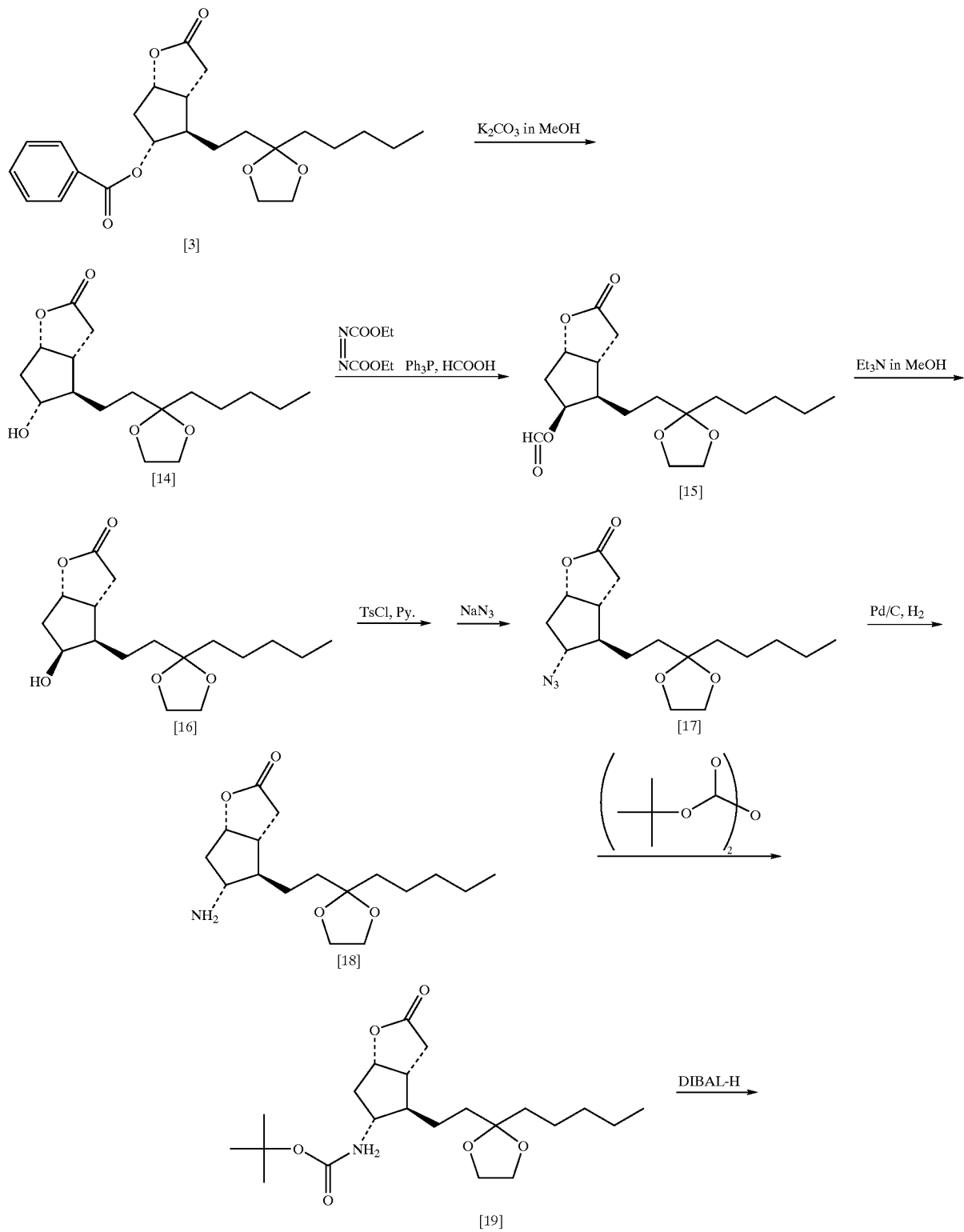

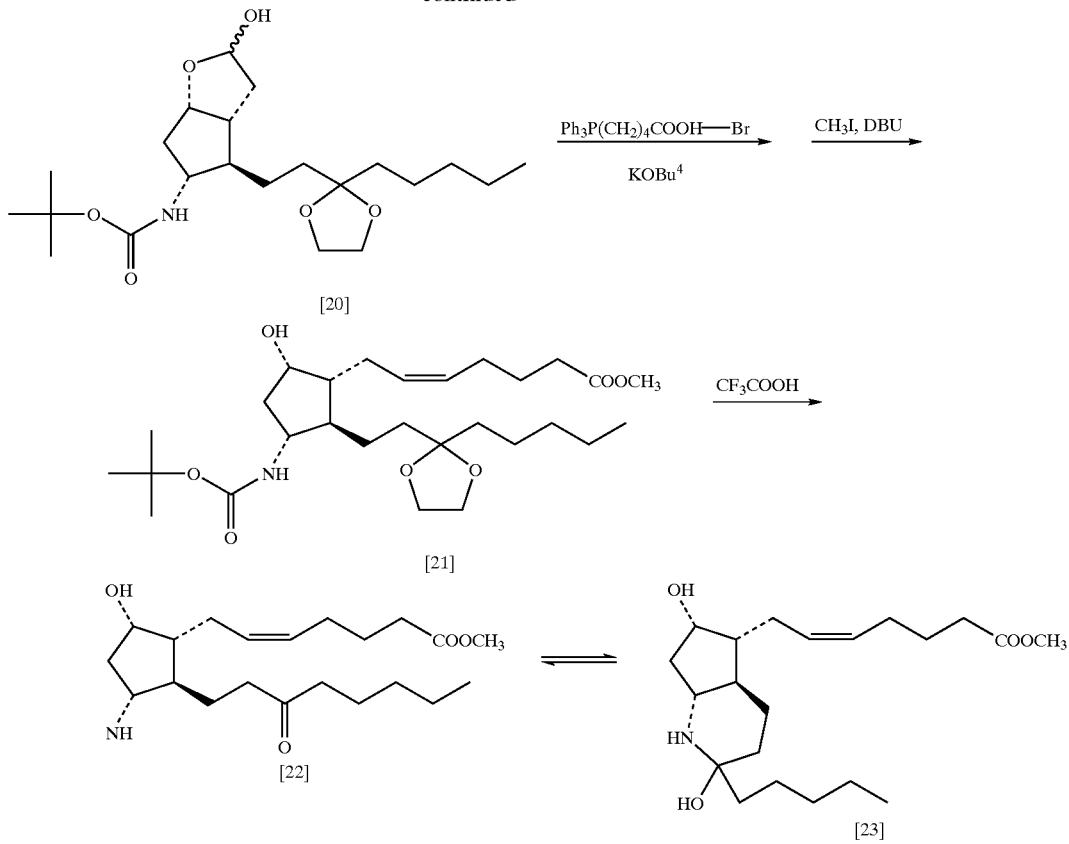
Another theoretical synthesis of a compound represented by Formula (I) where Z is a nitrogen atom is set forth below:
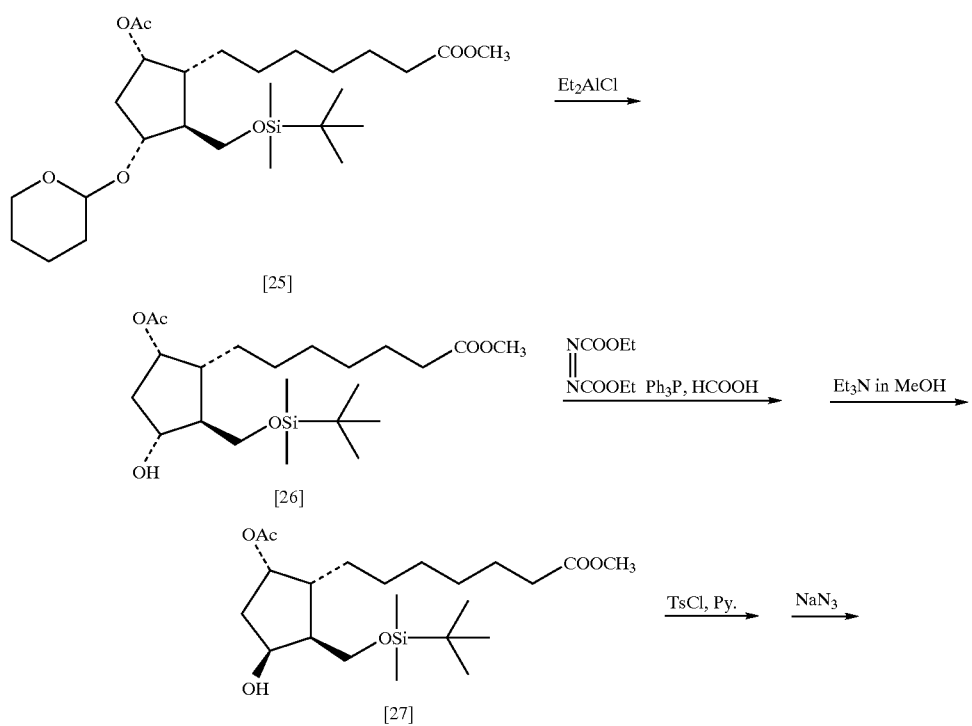

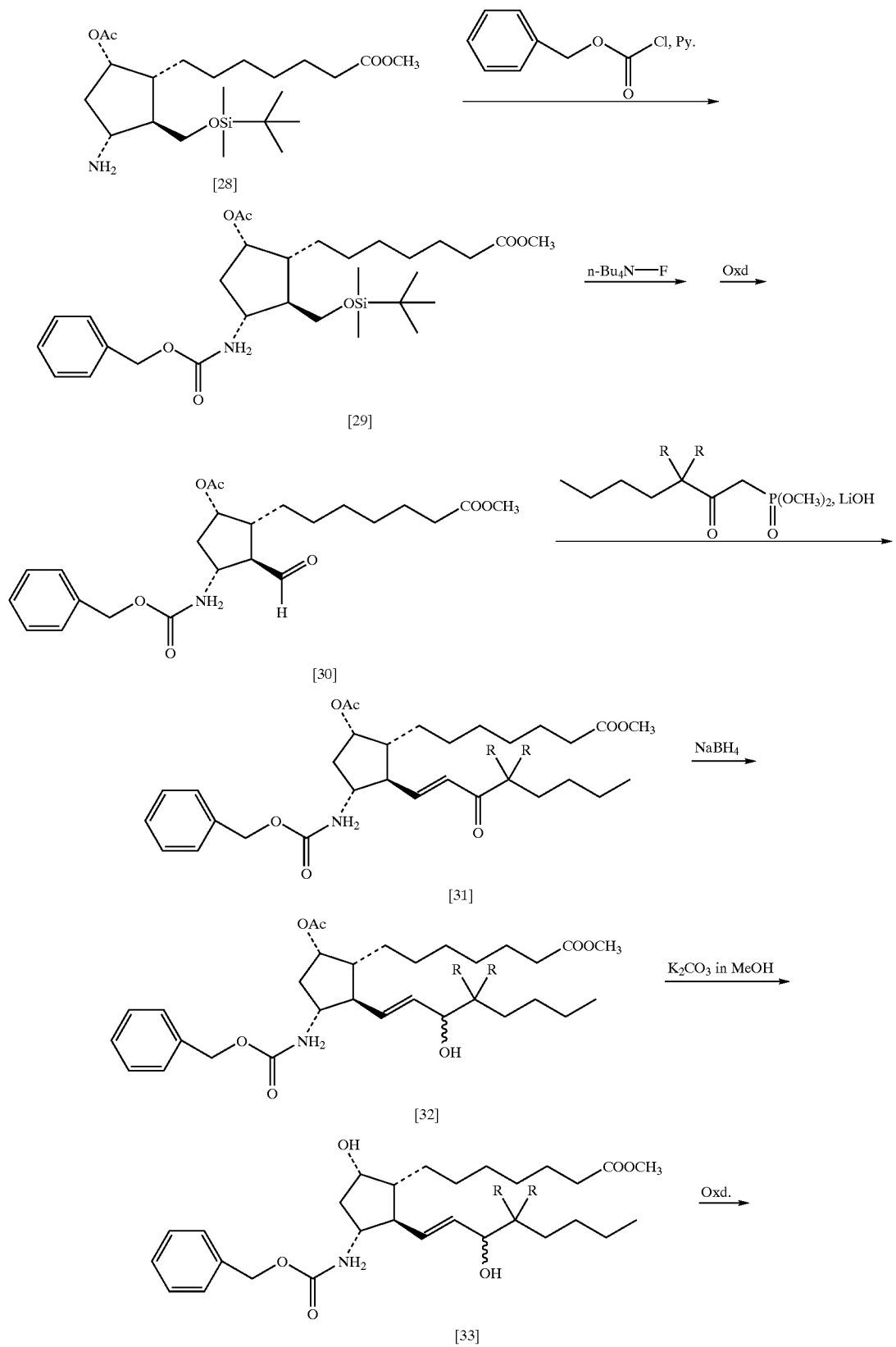

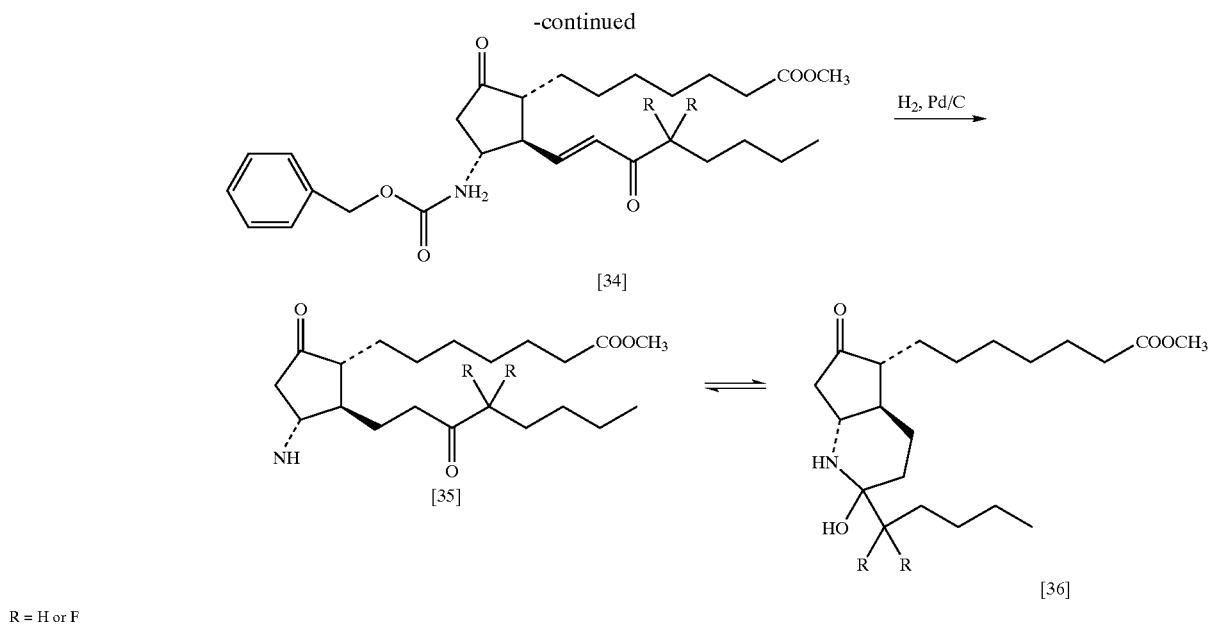

[34]

[35]

[36]

R = H or F

The preparations in the present invention are not construed to be limited to them, and suitable means for protection, oxidation, reduction and the like may be employed.

In the bi-cyclic-16-halogen compounds used in the present invention, enteropooling activity is remarkably enhanced when substituted by two halogen atoms, especially fluorine atoms, at the C-16 position independently of the structure and substituents of the five-membered ring or the existence of the double bonds or other substituents. Particularly preferable bi-cyclic-16-halogen compounds are those tautomers formed from mono-cyclic compounds having a ketone at the C-9 position and a hydroxyl group at the C-11 position in the five membered ring. Another preferable group is a bi-cyclic-16-halogen compound containing a 5,6-single bond, 5,6-double bond or those having the carbon number 20–22 where $R_1$ contains 4 to 6 carbon atoms preferably in a straight chain.

An example of a mono-cyclic/bi-cyclic-16-halogen compound containing a 5,6-double bond are set forth below:

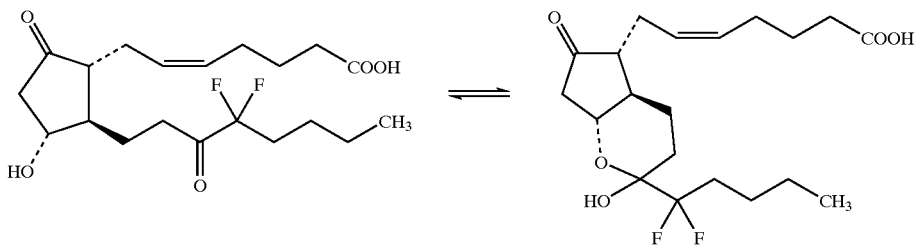

Another embodiment of the present invention comprises the composition of the present invention and a medium chain fatty acid triglyceride. The triglyceride may be a saturated or unsaturated fatty acid having 6–14 carbon atoms that may have a branched chain. A preferred fatty acid is a straight chain saturated fatty acid, for example, caproic acid, caprylic acid, capric acid, lauric acid and myristic acid. 2 or more medium chain fatty acid triglycerides may be used as a mixture.

The composition of the present invention may be dissolved or admixed in the medium chain fatty acid triglyceride. The amount of the medium chain fatty acid triglyceride is not limited. However, generally, 1–1,000,000 parts by weight of the medium chain fatty acid triglyceride based on one part by weight of the bi-cyclic structure may be used. Preferably, 5–500,000 parts by weight, and more preferably 10–200,000 parts by weight.

Examples of the medium chain fatty acid triglyceride used in the present 25 invention include a triglyceride of a saturated or unsaturated fatty acid having 6–14 carbon atoms which may have a branched chain. Preferred fatty acid is a straight chain saturated fatty acid for example caproic acid (C6), caprylic acid (C8), capric acid (C10), lauric acid (C12) and myristic acid (C14). In addition, 2 or more medium chain fatty acid triglycerides may be used.

Even more non-polar solvents, such as commercially available Miglyol can be employed to increase the bi-cyclic/mono-cyclic ratio.

To exemplify formulation of an embodiment of the present invention and to illustrate potential effect of steric hinderance, an Example is set forth.

EXAMPLE

The following compounds 1 and 2 were dissolved in a medium chain fatty acid triglyceride (MCT=mixture of caprylic acid triglyceride and capric acid triglyceride in a ratio of 85:15) in an amount shown in the table below.

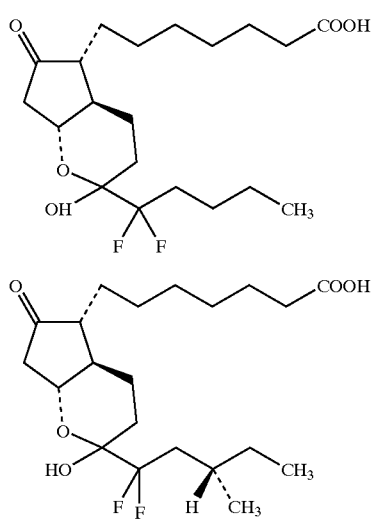

Each of the solutions was placed in a container made of hard glass and stored at 40° C. The time-course content of compound 1 and 2 in the solutions were determined by HPLC method. At the same time, each of compounds 1 and 2 was placed solely (without being dissolved in the solvent) in the container as above, and stored at 40° C. to provide control study.

(1) In the absence of the solvent, the content of the compounds was determined as follows by the HPLC method.

Stored compounds 1 and 2, and standard compounds 1 and 2 were weighed precisely around 0.025 g each, and exactly 5 mL aliquots of internal standard solution were added to the respectively weighed compounds. Test and standard preparations were obtained by adding acetonitrile (liquid chromatograph grade) to give the precise total amount of 10 mL each. Each 10 μL of the test and standard preparations were loaded on liquid chromatograph and determined the content of the compound by internal standard method with one $$\text{content (\%)} = \frac{Q_T}{Q_S} \times W_S \times \frac{100}{W_T}$$

$W_X$: The amount of the compound in the standard preparation (mg)
$W_T$: The amount of compound 1 and 2 in the test preparation.
$Q_S$: Peak area ratio of the compound in the standard preparation to the internal standard.
$Q_T$: Peak area ratio of the compound in the test preparation to the internal standard.

Measurement conditions:

Detector: Ultraviolet absorption spectrophotometer (wavelength 294 nm)
Column: A stainless tube having about 5 mm of internal diameter and about 25 cm of length, packed with 5 μm octadecylsilyl silica gel for liquid chromatograph
Column temperature: Stable around 35° C.

Mobile phase: Mixed solution of acetonitrile (liquid chromatograph grade)/aqueous sodium acetate (0.01 mol/L)/glacial acetic acid (800:200:1)

(2) In the presence of the solvent, the content of the compound was determined as follows by HPLC method.

Based on the value expressed in the above table, an amount of the solution corresponding to 36 μg of compounds 1 and 2 was weighed precisely. Precisely 1.0 mL of an internal standard solution was added, and then ethyl acetate (liquid chromatograph grade) was added to give a total amount of 10 mL each. Each 0.1 mL of the solution was vacuum concentrated to dryness to give the test preparation.

Each 18 mg of the standard compounds was weighed precisely and admixed with ethyl acetate (liquid chromatograph grade) to give the total amount of exactly 50 mL each. 1.0 mL of the solution and 10.0 mL of the internal standard solution were measured precisely and admixed with ethyl acetate (liquid chromatograph grade) to give a total of 100 mL each. Each 0.1 mL of the solution was vacuum concentrated to dryness to give the standard preparation.

To the test and standard preparations, 0.1 mL of fluorescent labeling reagent and 0.85 mL of fluorescent labeling catalyst were added, respectively, and the mixture was stirred and reacted at room temperature for more than 30 minutes. 0.05 mL aliquots of acetonitrile (liquid chromatograph grade) containing 2% acetic acid were added to the reaction mixtures, respectively, stirred, and then allowed to stand for more than 30 minutes to provide test and standard solutions.

Each 10 μL of the test and standard solution was loaded on liquid chromatograph and determined the content of the respective compounds by internal standard method with one point calibration curve.

$$\text{content (\%)} = \frac{Q_T}{Q_S} \times W_S \times \frac{100}{18}$$

$W_X$: The amount of the compound in the standard preparation (mg)
$Q_S$: Peak area ratio of the compound in the standard preparation to the internal standard.
$Q_T$: Peak area ratio of the compound in the test preparation to the internal standard.

Measurement conditions:

Detector: Fluorescent spectrometer (excitation wavelength 259 nm; fluorescent wavelength 394 nm)
Column: A stainless tube having about 5 mm of internal diameter and about 25 cm of length, packed with 5 μm octadecylsilyl silica gel for liquid chromatograph
Column temperature: Stable at around 35° C.
Mobile phase: Mixed solution of acetonitrile (liquid chromatograph grade)/methanol (liquid chromatograph grade)/ aqueous ammonium acetate (0.05 mol/L) (4:11:5)

|  |  | initial | 6 days | 7 days | 14 days | 28 days | 38 days | 90 days | 191 days |
| --- | --- | --- | --- | --- | --- | --- | --- | --- | --- |
| compound 1 | crystal | 100 |  | 97.2 | 94.1 | 87.4 |  |  |  |
|  | MCT[1] | 100 |  |  | 101.4 |  | 102.1 | 100.9 |  |
| compound 2 | crystal | 100 | 84.5 |  | 75.0 | 53.4 |  |  |  |
|  | MCT[2] | 100 |  |  | 99.6 | 98.9 |  |  | 99.6 |

[1]compound 1/solvent: 0.36 mg/g
[2]compound 2/solvent: 0.12 mg/g

The composition of the present invention causes extremely great enteropooling effect, inhibiting absorption of water in intestines. Further, the present compounds have no or greatly reduced, if any, intestinal contraction effect which PGEs or PGFs may possess. Therefore, the present composition treats constipation without malaise in belly owing to the intestinal contraction, such as bellyache. In addition, the present compound allows constipation to subside effecting normal bowl conditions. Moreover, it requires little time to recover from diarrhea symptoms if caused by the present compounds which possess great promotion effect of intraintestinal transportation. Therefore, they are even very useful as cathartics.

The composition of the present invention can be used as constipation treatment and prevention remedies for animals and humans, and, in general, used for systemic or local applications by oral administration, or as suppository, enema and the like. Sometimes, they may be applied as intravenous or subcutaneous injection. The dosage varies depending on animals, humans, age, weight, conditions, therapeutic effect, administration route, treatment time and the like. Preferably, it is 0.001–1,000 $\mu$g/kg, and more preferably 0.01 to 100 $\mu$g/kg.

The solid composition for oral administration of the present invention includes tablets, preparations, granules and the like. In such a solid composition, one or more active ingredients may be mixed with at least one inactive diluent, for example, lactose, mannitol, glucose, hydroxypropyl cellulose, microcrystalline cellulose, starch, polyvinyl pyrrolidone, magnesium aluminate metasilicate and the like. According to the usual work-up, the composition may contain additives other than inactive diluent, for example, lubricant such as magnesium stearate; disintegrant such as fibrous calcium gluconate; stabilizer such as cyclodextrin, for example, $\alpha,\beta$- or $\gamma$-cyclodextrin; etherified cyclodextrin such as dimethyl-$\alpha$-, dimethyl-$\beta$-, trimethyl-$\beta$- or hydroxypropyl-$\beta$-cyclodextrin; branched cyclodextrin such as glucosyl-, maltosyl-cyclodextrin; formylated cyclodextrin, cyclodextrin containing sulfur; phospholipid and the like. When the above cyclodextrins are used, inclusion compound with cyclodextrins may be sometimes formed to enhance stability. Alternatively, phospolipid may be sometimes used to form liposome, resulting in enhanced stability.

Tablets or pills may be coated with film soluble in the stomach or intestine such as sugar, gelatin, hydroxypropyl cellulose, hydroxypropylmethyl cellulose phthalate as needed. Further, they may be formed as capsules with absorbable substances such as gelatin.

A liquid composition for oral administration may contain pharmaceutically acceptable emulsion, solution, suspension, syrup, elixir as well as generally used inactive diluent. Such composition may contain, in addition to the inactive diluent, adjuvants such as suspensioning agents, sweetening agents, flavoring agents, preservatives, solubilizers, anti-oxidants and the like. The details of the additives may be selected from those described in any general textbooks in the pharmaceutical field. Such liquid compositions may be directly enclosed in soft capsules. However, the selection of a diluent other than those mentioned above, which the bi-cyclic/mono-cyclic compound may be dissolved or admixed in, must carefully be selected so as not to affect the bi-cyclic/mono-cyclic ratio.

Solutions for parenteral administration, for example, suppository, enema and the like according to the present invention include steril, aqueous or non-aqueous solution, suspension, emulsion and the like. The aqueous solution and suspension includes, for example, distilled water, physiological saline and Ringer's solution.

The non-aqueous solution and suspension include, for example, propylene glycol, polyethylene glycol, fatty acid triglyceride, vegetable oil such as olive oil, alcohols such as ethanol, polysorbate and the like. Such composition may contain adjuvants such as preservatives, wetting agent, emulsifier, dispersant, anti-oxidants and the like.

The present invention will be illustrated in the following examples. Which are illustrated by way of example only and not intended to limit the scope of the present invention.

Correlation of Mono-cyclic/bi-cyclic Structure and Biological Activity

To exemplify the effect of halogenated-bi-cyclic compounds with halogen atoms at the C-16 position in the composition of the present invention, the following Examples were prepared and tested.

Example 1

The biological activity of compositions due to the ratios of mono-cyclic/bi-cyclic structures when Z of general formula (I) is an oxygen atom, and a ketone is present at the C-9 position of the present invention can be seen from the following examples. The number of fluorine atoms at the C-16 position and the ratio of mono-cyclic/bi-cyclic structures are shown in Table 1.

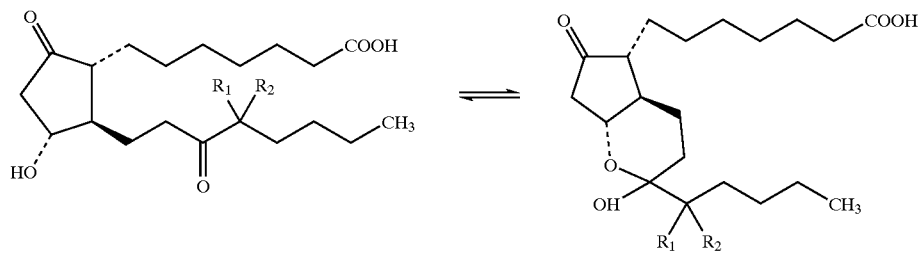

Enteropooling tests and diarrhea tests were conducted. The results are set forth in Table 1. The dose that raise the intraintestinal content by 50% was referred to as $ED_{50}$.

Enteropooling tests and diarrhea tests were conducted. The results are set forth below in Table 2. The dose that raise the intraintestinal content by 50% was referred to as $ED_{50}$.

TABLE 1

|  | Example A | Example B | Comparative Example A |
|---|---|---|---|
| Number of F atoms at C-16 position | 2 | 1 | 0 |
| Ratio of mono-cyclic/bi-cyclic structure* | 4:96 | 1:1 | No signal derived from bi-cyclic structure was detected. |
| Enteropooling activity, $ED_{50}$ | 0.6 µg/kg | 2 µg/kg | 320 µg/kg |
| Diarrhea in mice | +: at 3 mg/kg (PO[1]) +: at 0.3 mg/kg (SC[2]) | ±: at 0.3 mg/kg (SC) | −: at 10 mg/kg (PO) −: at 1 mg/kg (SC) |

*Determined by NMR measurement in $CDCl_3$ solution.
[1]PO is by mouth (oral administration)
[2]SC is subcutaneous administration Example 2

The biological activity of the composition due to the ratios of mono-cyclic/bi-cyclic structures when Z in Formula (I) is an oxygen, a ketone is present at the C-9 position, and there is a double bond between the 5,6-carbons is shown below.

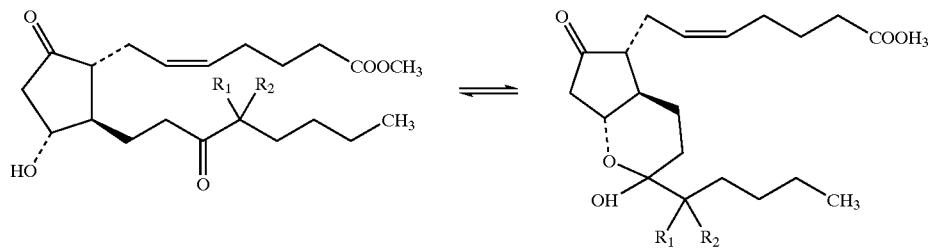

TABLE 2

|  | Example C | Example D | Comparative Example C |
|---|---|---|---|
| Number of F atoms at C-16 position | 2 | 1 | 0 |
| Ratio of mono-cyclic/bi-cyclic structure* | 4:96 | 1:1 | no signal derived from bi-cyclic structure was detected. |
| Enteropooling activity, $ED_{50}$ | 0.3 µg/kg | 3 µg/kg | 220 µg/kg |

TABLE 2-continued

|  | Example C | Example D | Comparative Example C |
|---|---|---|---|
| Diarrhea in mice | +: at 1 mg/kg (PO)[1] | −: at 1 mg/kg (PO)<br>+: at 5 mg/kg (PO) | −: at 10 mg/kg (PO) |

\* Determined by NMR measurement in CDCl$_3$ solution.
[1]PO is by mouth (oral administration)

Effect of the Present Invention Dissolved in Medium Chain Fatty Acid Triglyceride on Bowel Movement After Single Oral Administration to Healthy Male Volunteers 3 to 9 healthy male volunteers were treated with a composition containing the following mono-cyclic/bi-cyclic structures (in CDCl$_3$) in a ratio of 4:96.

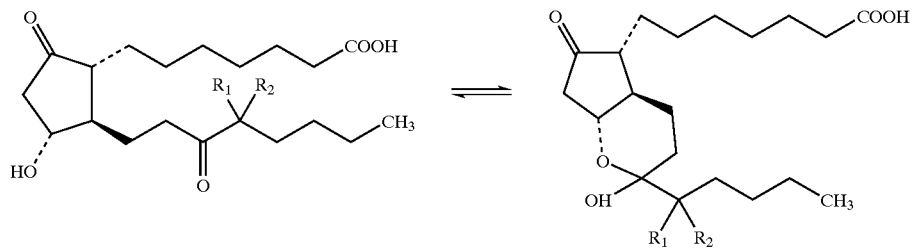

The test substance (R$_1$ and R$_2$ are F atoms) was dissolved in Panacet 800 (medium chain fatty acid triglyceride manufactured by Nippon Oil & Fat co., Ltd., Amagasaki, Japan) and filled in a capsule (each capsule contains 200 L of the mixture). Each subject was administered one capsule with 100 mL of water.

Table 3 shows the number of subjects who experienced loose stool or diarrhea.

TABLE 3

| | Number of Subjects | |
|---|---|---|
| Dose | Normal | Loose or Diarrhea |
| 5 μg | 1/3 | 2/3 |
| 10 μg | 5/7 | 2/7 |
| 20 μg | 1/3 | 2/3 |
| 30 μg | 2/9 | 7/9 |

While the invention has been described in detail and with reference to specific embodiments thereof, it will be apparent to one skilled in the art that various changes and modifications can be made therein without departing from the spirit and scope thereof.

What is claimed is:

1. A method for relieving or preventing constipation in a human constipated patient or cleansing a bowel of a patient which comprises administering to the patient a therapeutically effective amount of the pharmaceutical composition comprising in an amount sufficient for relieving or preventing constipation in a human constipated patient or cleansing a bowel of a human patient a bi-cyclic compound represented by formula (I):

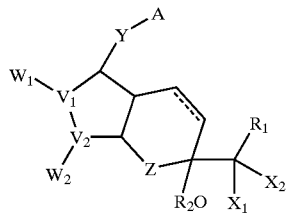

where V$_1$ and V$_2$ are carbon atoms;
W$_1$ and W$_2$ are

R$_3$ and R$_4$ are hydrogen atoms or one of them is OH;
X$_1$ and X$_2$ are hydrogen, lower alkyl or halogen atom, and at least one of these is a halogen atom;
Z is an oxygen atom;
R$_2$ is a hydrogen atom or alkyl;
Y is a saturated or unsaturated C$_{2-10}$ hydrocarbon chain which is unsubstituted or substituted by oxo, halogen, an alkyl group, hydroxyl or aryl;
A is -CH$_2$OH, -COCH$_2$OH, -COOH or its functional derivative; and
R$_1$ is a saturated or unsaturated, lower hydrocarbon forming a straight-chain, a branched-chain or a ring, which is unsubstituted or substituted by halogen, oxo, hydroxy, lower alkoxy, lower alkanoyloxy, lower cycloalkyl, lower cycloalkyloxy, aryl, or aryloxy; lower cycloalkyl; lower cycloalkyloxy; aryl or aryloxy,
a bond between C-13 and C-14 position can be a double or single bond, and C-15 can have a steric configuration of R, S, or a mixture thereof, and a compound which is a mono-cyclic tautomer of formula (I), wherein in the composition a ratio of the bi-cyclic compound to the mono-cyclic tautomer is at least 1:1.

2. A method for relieving or preventing constipation in a human constipated patient or cleansing a bowel of a patient which comprises administering to the patient a therapeutically effective amount of the pharmaceutical composition comprising a bi-cyclic compound represented by the following Formula (I);

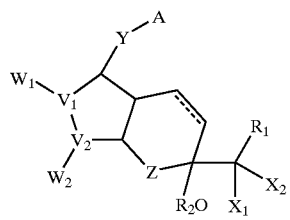

where $V_1$ and $V_2$ are carbon atoms;
$W_1$ and $W_2$ are

$R_3$ and $R_4$ are hydrogen atoms or one of them is OH;
$X_1$ and $X_2$ are hydrogen, lower alkyl or halogen atom, and at least one of these is a halogen atom;
Z is an oxygen atom;
$R_2$ is a hydrogen atom or alkyl;
Y is a saturated or unsaturated $C_{2-10}$ hydrocarbon chain which is unsubstituted or substituted by oxo, halogen, an alkyl group, hydroxyl or aryl;
A is -CH$_2$OH, -COCH$_2$OH, -COOH or its functional derivative; and
$R_1$ is a saturated or unsaturated, lower hydrocarbon forming a straight-chain, a branched-chain or a ring, which is unsubstituted or substituted by halogen, oxo, hydroxy, lower alkoxy, lower alkanoyloxy, lower cycloalkyl, lower cycloalkyloxy, aryl, or aryloxy; lower cycloalkyl; lower cycloalkyloxy; aryl or aryloxy, a bond between C-13 and C-14 position can be a double or single bond, C-15 can have a steric configuration of R, S, or a mixture thereof, a compound which is a mono-cyclic tautomer of formula (I);

and a medium chain fatty acid triglyceride, wherein in the composition a ratio of the bi-cyclic compound to the monocyclic tautomer is at least 1:1.

3. The method according to claim 1, wherein in the composition a ratio of bi-cyclic/mono-cyclic structure is at least 20:1.

4. The method according to claim 1, wherein A is -COOH, $W_1$ is a ketone, $R_2$ is a hydrogen atom, and $X_1$ and $X_2$ are fluorine atoms.

5. The method according to claim 1, wherein A is COOH; Y is (CH$_2$)$_6$; $W_1$ is =O; $R_3$ and $R_4$ are hydrogen atoms; $X_1$ and $X_2$ are fluorine atoms; and $R_1$ is (CH$_2$)$_3$CH$_3$.

6. The method according to claims 2, wherein the ratio of bi-cyclic/mono-cyclic structure is at least 20:1.

7. The method according to claim 2, wherein A is -COOH, $W_1$ is a ketone, and $X_1$ and $X_2$ are fluorine atoms.

8. The method according to claim 2, wherein A is COOH; Y is (CH$_2$)$_6$; $W_1$ is =O; $R_3$ and $R_4$ are hydrogen atoms; $X_1$ and $X_2$ are fluorine atoms; and $R_1$ is (CH$_2$)$_3$CH$_3$.

9. The method according to claim 2, wherein the medium chain fatty acid triglyceride is present in an amount of 1–1,000,000 parts by weight based on one part by weight of the bi-cyclic structure.

10. The method according to claim 9, wherein the medium chain fatty acid triglyceride is present in an amount of 5–500,000 parts by weight based on one part by weight of the bi-cyclic structure.

11. The method according to claim 9, wherein the medium chain fatty acid triglyceride is present in an amount of 10–200,000 parts by weight based on one part by weight of the bi-cyclic structure.

12. The method according to claim 2, wherein the medium chain fatty acid triglyceride is a triglyceride of a fatty acid having 6–14 carbon atoms.

13. The method according to claim 2, wherein the medium chain fatty acid triglyceride is caprylic acid triglyceride and/or capric triglyceride.

* * * * *